(12) United States Patent
Weichselbaum et al.

(10) Patent No.: US 7,247,297 B2
(45) Date of Patent: Jul. 24, 2007

(54) USE OF DF3/MUC1 REGULATED EXPRESSION IN GENE THERAPY

(75) Inventors: Ralph R. Weichselbaum, Chicago, IL (US); Donald W. Kufe, Wellesley, MA (US)

(73) Assignees: The University of Chicago, Chicago, IL (US); Dana-Farber Cancer Institute, Boston, MA (US)

( * ) Notice: Subject to any disclaimer, the term of this patent is extended or adjusted under 35 U.S.C. 154(b) by 248 days.

(21) Appl. No.: 10/244,705

(22) Filed: Sep. 16, 2002

(65) Prior Publication Data

US 2003/0091539 A1 May 15, 2003

Related U.S. Application Data

(60) Provisional application No. 60/322,265, filed on Sep. 14, 2001.

(51) Int. Cl.
*A61K 48/00* (2006.01)
*A01N 63/00* (2006.01)

(52) U.S. Cl. .................................... 424/93.2
(58) Field of Classification Search ............... 424/93.2; 435/320.1, 455, 456
See application file for complete search history.

(56) References Cited

U.S. PATENT DOCUMENTS

| | | | |
|---|---|---|---|
| 5,506,343 A | 4/1996 | Kufe | 530/387.7 |
| 5,712,136 A | 1/1998 | Wickham et al. | 435/172.3 |
| 5,744,144 A | 4/1998 | Finn et al. | 424/277.1 |
| 5,772,995 A | 6/1998 | Fakharai et al. | 424/93.21 |
| 5,783,567 A | 7/1998 | Hedley et al. | 514/44 |
| 5,807,978 A | 9/1998 | Kokolus et al. | 530/300 |
| 5,817,481 A * | 10/1998 | Rood | 435/69.1 |
| 5,821,080 A | 10/1998 | Everett et al. | 435/69.1 |
| 5,827,666 A | 10/1998 | Finn et al. | 435/7.1 |
| 5,846,746 A | 12/1998 | Gipson | 435/7.21 |
| 5,856,112 A | 1/1999 | Marley et al. | 435/7.23 |
| 5,858,360 A | 1/1999 | Fukuda | 424/130.1 |
| 5,876,735 A | 3/1999 | Reed | 424/269.1 |
| 5,879,687 A | 3/1999 | Reed | 424/269.1 |
| 5,880,267 A | 3/1999 | Fukuda | 530/387.1 |
| 5,885,806 A | 3/1999 | Dropulic et al. | 435/91.41 |
| 5,888,497 A | 3/1999 | Jain et al. | 424/93.7 |
| 5,888,767 A | 3/1999 | Dropulic et al. | 435/69.1 |
| 5,891,432 A | 4/1999 | Hoo | 424/93.21 |
| 5,891,651 A | 4/1999 | Roche et al. | 435/7.21 |
| 5,910,451 A | 6/1999 | Fukuda | 436/501 |
| 5,922,836 A | 7/1999 | Watson et al. | 530/300 |
| 5,925,568 A | 7/1999 | Comer et al. | 435/378 |
| 5,929,222 A | 7/1999 | Lindemann et al. | 536/23.4 |
| 5,962,311 A | 10/1999 | Wickham et al. | 435/320.1 |
| 5,965,381 A | 10/1999 | van der Bruggen et al. | 435/29 |
| 6,001,349 A | 12/1999 | Panicali et al. | 424/93.2 |
| 6,013,268 A | 1/2000 | Reed | 424/269.1 |
| 6,045,802 A | 4/2000 | Schlom et al. | 424/199.1 |
| 6,051,218 A | 4/2000 | McBride | 424/93.21 |
| 6,054,312 A | 4/2000 | Larocca et al. | 435/320.1 |
| 6,060,064 A | 5/2000 | Adams et al. | 424/199.1 |
| 6,070,126 A | 5/2000 | Kokolus et al. | 702/19 |
| 6,080,725 A | 6/2000 | Marciani | 514/26 |
| 6,111,087 A | 8/2000 | Rethwilm et al. | 536/23.4 |
| 6,114,129 A | 9/2000 | Agrawal et al. | 435/7.24 |
| 6,114,141 A | 9/2000 | Dropulic et al. | 435/69.1 |
| 6,120,763 A | 9/2000 | Fakhrai et al. | 424/93.21 |
| 6,432,700 B1 * | 8/2002 | Henderson et al. | 435/320.1 |
| 6,841,538 B1 * | 1/2005 | Joshi et al. | 514/44 |
| 2002/0045261 A1 * | 4/2002 | Snyder et al. | 435/368 |
| 2003/0068307 A1 * | 4/2003 | Yu et al. | 424/93.21 |

OTHER PUBLICATIONS

Vile et al., Gene Therapy, vol. 7, pp. 2-8, 2000.*
Verma, Nature, vol. 389, pp. 239-242, 1997.*
Anderson et al., Nature, vol. 392, pp. 25-30, Apr. 1998.*
Ring et al. Gene Therapy, 4:1045-1052, 1997.*
Abe and Kufe, "Characterizaton of cis-acting elements regulating transcription of the human DF3 breast carcinoma-associated antigen (MUCI) gene," *Proc. Nat'l Acad. Sci. U.S.A.*, 90:282-286, 1993.
Abe and Kufe, "Identification of a family of high molecular weight tumor-associated glycoproteins," *J. Immunol.*, 139:257-261, 1987.
Abe and Kufe, "Transcriptional regulation of DF3 gene expression in human MCF-7 breast carcinoma cells," *J. Cell. Physiol.*, 143:226-231, 1990.
Advani et al., "Replication-competent, nonneuroinvasive genetically engineered herpes virus is highly effective in the treatment of therapy-resistant experimental human tumors," *Cancer Res.*, 59:2055-2058, 1999.
Batra et al., "Transfection of the human MUC 1 mucin gene into a poorly differentiated human pancreatic tumor cell line, Panel: integration, expression and ultrastructural changes," *J. Cell Sci.*, 100:841-849, 1991.
Berglund et al., "Semliki Forest virus expression system: production of conditionally infectious recombinant particles," *Biotechnology*, 11:916-920, 1993.
Botti et al., "Effects of steroid-free fetal serum and steroid supplementation on MUC1 gene expression in human breast cancer cell line MCF7," *Anticancer Res.*, 17:205-208, 1997.
Chen et al., "Breast cancer selective gene expression and therapy mediated by recombinant adenoviruses containing the DF3/MUC1 promoter," *J. Clin. Invest.*, 96:2775-2782, 1995.

(Continued)

*Primary Examiner*—Brian Whiteman
(74) *Attorney, Agent, or Firm*—Michael Best & Friedrich LLP

(57) ABSTRACT

The present invention provides for improved vectors for use in gene therapy. Utilizing the cancer specific DF3/MUC1 promoter to drive a replication essential gene, vectors are made conditionally replication-competent, permitting wider infection and expression of tumor cells. In addition, therapeutic genes and adjunct therapies further increase anti-tumor efficacy.

2 Claims, 3 Drawing Sheets

OTHER PUBLICATIONS

Chmura et al., "Strategies for enhancing viral-based gene therapy using ionizing radiation," *Radiat. Oncol. Investig.*, 7:261-269, 1999.

Dion et al., "E1A RNA transcripts amplify adenovirus-mediated tumor reduction," *Gene Ther.*, 3:1021-1025, 1996.

Friedman et al., "Reactivity of monoclonal antibody DF3 with a high molecular weight antigen expressed in human ovarian carcinoma," *Cancer Res.*, 46:5189-5194, 1986.

Hareuveni et al., "Vaccination against tumor cells expressing breast cancer epithelial tumor antigen," *Proc. Nat'l Acad. Sci. U.S.A.*, 87:9498-9502, 1990.

Heise and Kirn, "Replication-selective adenoviruses as oncolytic agents," *J. Clin. Invest.*, 105:847-851, 2000.

Ho et al., "Heterogeneity of Mucin gene expression in normal and neoplastic tissues," *Cancer Res.*, 53:641-651, 1993.

Jarrard et al, "MUC1 is a novel marker for the type II pneumocyte lineage during lung carcinogenesis," *Cancer Res.*, 58:5582-5588, 1998.

Kufe et al., "Differential reactivity of a novel monclonal antibody (DF3) with human malignant versus benign breast tumors," *Hybridoma*, 3:223-232, 1984.

Kurihara et al., "Selectivity of a replication-competent adenovirus for human breast carcinoma cells expressing the MUC1 antigen," *J. Clin. Invest.*, 106:763-771, 2000.

Lancaster et al., "Structure and expression of the human polymorphic epithelial mucin gene: expressed VNRT unit," *Biochem. Biophys. Res. Commun.*, 173:1019-1029, 1990.

Manome et al., "Enhancer sequences of the DF3 gene regulate expression of the herpes simplex virus thymidine kinase gene and confer sensitivity of human breast cancer cells to ganiciclovir," *Cancer Res.*, 54:5408-5413, 1994.

Metzgar et al., "Detection of a pancreatic cancer-associated antigen (DU-PAN-2 antigen) in serum and ascites of patients with adeoncarcinoma," *Proc. Nat'l Acad. Sci. USA*, 81:5242-5246, 1984.

Miyatake et al., "Hepatoma-specific antitumor activity of an albumin enhancer/promoter regulated herpes simplex virus in vivo," *Gene Ther.*, 6:564-572, 1999.

Parker et al., "From the cover: engineered herpes simplex virus expressing IL-12 in the treatment of experimental murine brain tumors," *Proc. Natl. Acad. Sci. USA*, 97:2208-2213, 2000.

Patterson and Harris, "Molecular chemotherapy for breast cancer," *Drugs Aging*, 14:75-90, 1999.

Rodriguez et al., "Prostate attenuated replication competent adenovirus (ARCA) CN706: a selective cytotoxic for prostate-specific antigen-positive prostate cancer cells," *Cancer Res.*, 57:2559-2563, 1997.

Smyth et al., "Use of the 5'-flanking region of the mouse perforin gene to express human Fc gamma receptor I in cytotoxic T lymphocytes," *J. Leukoc Biol.*, 55:514-522, 1994.

Spicer et al., "Molecular cloning and analysis of the mouse homologue of the tumor-associated mucin, MUC1, reveals conservation of potential O-glycosylation sites, transmembrane, and cytoplasmic domains and a loss of minisatellite-like polymorphism," *J. Biol. Chem.*, 266:15099-15109, 1991.

Swallow et al., "The hypervariable gene locus PUM, which codes for the tumour associated epithelial mucins, is located on chromosome 1, within the region 1q21-24," *Ann. Hum. Genet.*, 51:289-294, 1987.

Todo et al., "Corticosteroid administration does not affect viral oncolytic activity, but inhibits antitumor immunity in replication-competent herpes simplex virus tumor therapy," *Hum Gene Ther.*, 10:2869-2878, 1999.

Todo et al., "Systemic antitumor immunity in experimental brain tumor therapy using a multimutated, replication-competent herpes simplex virus," *Hum Gene Ther.*, 10:2741-2755, 1999.

Treon et al., "MUC-1 core protein is expressed on multiple myeloma cells and is induced by dexamethasone," *Blood*, 93:1287-1298, 1999.

Uchida, "In vivo suicide gene therapy model using a newly discovered prostate-specific membrane antigen promoter/enhancer: a potential alternative approach to androgen deprivation therapy," *Urology*, 58(2 Suppl 1):132-139, 2001.

Varda-Bloom, "Tissue-specific gene therapy directed to tumor angiogenesis," *Gene Ther.*, 8(11):819-827, 2001.

Wegner et al., "Tyrosine kinase inhibition decrease MUC-1 expression in mouse epithelial cells," *J. Cell Physiol.*, 170:200-208, 1997.

Zhou et al., "Estrogen receptor does not directly regulate the murine MUC-1 promoter," *Mol Cell Endocrinol.*, 143:65-78, 1998.

* cited by examiner

USE OF DF3/MUC1 REGULATED EXPRESSION IN GENE THERAPY

The present patent application claims priority to U.S. Provisional Patent Application Ser. No. 60/322,265, filed Sep. 14, 2001. The entire text of the above-referenced disclosure is specifically incorporated by reference herein without disclaimer.

BACKGROUND OF THE INVENTION

I. Field of the Invention

The present invention relates generally to the fields of oncology and molecular biology. More particularly, it concerns targeting of cancer cells expressing DF3/MUC1 antigens using a DF3/MUC1-regulated viral expression construct.

II. Description of Related Art

Recombinant adenoviruses have been used as highly efficient vectors for in vitro and in vivo gene transfer. Adenovirus-mediated gene transduction has been achieved in a broad spectrum of eukaryotic cells, and is independent of cell replication (Haj-Ahmad et al., 1986; Bett et al., 1994). In addition, E1 gene-deleted, replication-defective adenoviruses can accommodate large DNA inserts (Haj-Ahmad et al., 1986; Bett et al., 1994).

However, limitations of this vector system for cancer therapy have resulted in the non-selective delivery of therapeutic genes to both normal cells and tumor cells. Moreover, replication-defective adenoviruses are limited by their inability to infect and then spread to neighboring tumor cells. Strategies to circumvent these limitations involve the use of promoters or enhancers that are specific to or selective for tumor tissue in order to direct replication of the adenovirus in the desired target cells (Heise et al. 2000). In this context, the minimal promoter/enhancer from the prostate-specific antigen (PSA) gene has been used to drive E1A expression and thereby create an adenovirus, designated CN706, that selectively replicates in PSA-positive cells (Rodriguez et al., 1997). A similar strategy using the albumin promoter has been used to develop a herpes simplex virus that selectively replicates in hepatoma cells (Miyatake et al. 1999). Other tissue specific promoters include carcinoembryonic antigen (CEA) and alpha-feto protein (AFP).

Tissue specific promoters have also been used to drive the expression of therapeutic genes. For example PSMA, a type 2 membrane protein expressed in the prostate, is a useful target for prostate cancer therapy. The PSMA construct has been used to drive the suicide gene cytosine deaminase (Uchida et al., 2001). Another group has directed gene therapy specifically to vascular wall for treating vascular disease and cancer using the PPE-1 promoter (Varda-Bloom et al., 2001). The various types of tissue specific promoters/enhancers are described elsewhere in the specification.

In spite of these efforts, there remains a need in the art to construct vectors that can exploit the benefits of tissue specific gene expression in cancer cells.

SUMMARY OF THE INVENTION

Thus, in accordance with the present invention, there is provided a method for inhibiting the growth of a cancer cell that expresses DF3/MUC1 glycoprotein comprising, administering to the cell a polynucleotide comprising a nucleic acid segment encoding a product that inhibits the growth of a cancer cell operably linked to DF3/MUC1 glycoprotein specific promoter in combination with radiotherapy. The nucleic acid segment encodes a tumor suppressor, an inhibitor of apoptosis, a cell cycle regulatory gene, a toxin, a cytokine, a ribosome inhibitory protein. The toxin may be TNFα. The polynucleotide may be contained in a viral vector, for example, an adenoviral vector, a herpesviral vector, a vaccinia viral vector, a retroviral vector, an adeno-associated viral vector, or a lentiviral vector. The cancer cell may be a bladder cell, a breast cell, a lung cell, a colon cell, a prostate cell, a liver cell, a pancreatic cell, a stomach cell, a testicular cell, a brain cell, an ovarian cell, a lymphatic cell, a skin cell, a bone cell, a soft tissue cell. The cancer cell may be in a patient.

In another embodiment, there is provided an adenoviral vector comprising a polynucleotide comprising a nucleic acid segment encoding a product that inhibits the growth of a cancer cell operably linked to DF3/MUC1 glycoprotein specific promoter. The nucleic acid segment encodes a tumor suppressor, an inhibitor of apoptosis, a cell cycle regulatory gene, a toxin, a cytokine, a ribosome inhibitory protein.

In yet another embodiment, there is provided a method of treating a patient with cancer, cells of which express DF3/MUC1 (Accession Gene Bank L06162: SEQ ID NO:1), comprising administering to the patient a polynucleotide comprising a nucleic acid segment encoding a product that inhibits the growth of a cancer cell operably linked to DF3/MUC1 glycoprotein specific promoter in combination with radiotherapy. The nucleic acid segment encodes a tumor suppressor, an inhibitor of apoptosis, a cell cycle regulatory gene, a toxin, a cytokine, a ribosome inhibitory protein. The polynucleotide may be contained in a viral vector, for example, an adenoviral vector, a herpesviral vector, a vaccinia viral vector, a retroviral vector, an adeno-associated virals vector, or a lentiviral vector. The patient may have a bladder cancer, breast cancer, lung cancer, colon cancer, prostate cancer, liver cancer, pancreatic cancer, stomach cancer, testicular cancer, brain cell, ovarian cancer, lymphatic cancer, skin cancer, bone cancer, soft tissue cancer.

In still yet another embodiment, there is provided a method for inhibiting the growth of a cancer cell comprising, administering to the cell a viral vector wherein a replication essential gene of said viral vector is operably linked to a MUC1 promoter. The viral vector may be administered to the cell in combination with a second cancer therapy, such as radiotherapy, chemotherapy, immunotherapy, or gene therapy. The viral vector may be administered directly, regionally, parenterally, orally, intravenously, intraperitonealy, intratracheally, intramuscularly, subcutaneously, endoscopically, intralesionally, or percutaneously. The viral vector may further comprise a polynucleotide comprising a nucleic acid segment encoding a product that inhibits the growth of a cancer cell operably linked to a promoter. The promoter may be a CMV promoter, an RSV promoter, an LTR promoter, or a MUC1 promoter. If the promoter is a MUC1 promoter, it may be the same or different from that used to drive the replication essential gene. The nucleic acid segment may encode a tumor suppressor, an inhibitor of apoptosis, a cell cycle regulatory gene, a toxin, a cytokine, a ribosome inhibitory protein. The cancer cell may be a bladder cell, a breast cell, a lung cell, a colon cell, a prostate cell, a liver cell, a pancreatic cell, a stomach cell, a testicular cell, a brain cell, an ovarian cell, a lymphatic cell, a skin cell, a bone cell, a soft tissue cell. The cancer cell may be located in a patient. The viral vector may be an adenoviral vector, a herpesviral vector, a vaccinia viral vector, a retroviral vector, an adeno-associated viral vector, or a lentiviral vector.

In a further embodiment, there is provided a viral vector comprising a replication essential gene of said viral vector operably linked to a MUC1 promoter. The viral vector may comprise a polynucleotide that comprises a nucleic acid segment encoding a product that inhibits the growth of a cancer cell operably linked to a promoter. The promoter may be a CMV promoter, an RSV promoter, an LTR promoter, or a MUC1 promoter. The MUC1 promoter may be the same or different as that used to drive the replication essential gene. The nucleic acid segment may encode a tumor suppressor, an inhibitor of apoptosis, a cell cycle regulatory gene, a toxin, a cytokine, or a ribosome inhibitory protein. The viral vector may be an adenoviral vector, a herpesviral vector, a vaccinia viral vector, a retroviral vector, an adeno-associated viral vector, or a lentiviral vector.

In still a further embodiment, there is provided a method of treating a patient with cancer, comprising administering to the patient a viral vector wherein a replication essential gene of said viral vector is operably linked to a MUC1 promoter. The viral vector may be administered to the cell in combination with a second cancer therapy, such as radiotherapy, chemotherapy, immunotherapy, or gene therapy. The viral vector may be administered directly, regionally, parenterally, orally, intravenously, intraperitonealy, intratracheally, intramuscularly, subcutaneously, endoscopically, intralesionally, or percutaneously. The patient may have bladder cancer, breast cancer, lung cancer, colon cancer, prostate cancer, liver cancer, pancreatic cancer, stomach cancer, testicular cancer, brain cell, ovarian cancer, lymphatic cancer, skin cancer, bone cancer, soft tissue cancer. The viral vector may comprise a polynucleotide comprising a nucleic acid segment encoding a product that inhibits the growth of a cancer cell operably linked to a promoter. The promoter may be a CMV promoter, an RSV promoter, an LTR promoter, or a MUC1 promoter. The MUC1 promoter may be the same or different as that used to drive the replication essential gene. The nucleic acid segment may encode a tumor suppressor, an inhibitor of apoptosis, a cell cycle regulatory gene, a toxin, a cytokine, or a ribosome inhibitory protein. The viral vector may be an adenoviral vector, a herpesviral vector, a vaccinia viral vector, a retroviral vector, an adeno-associated viral vector, or a lentiviral vector.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
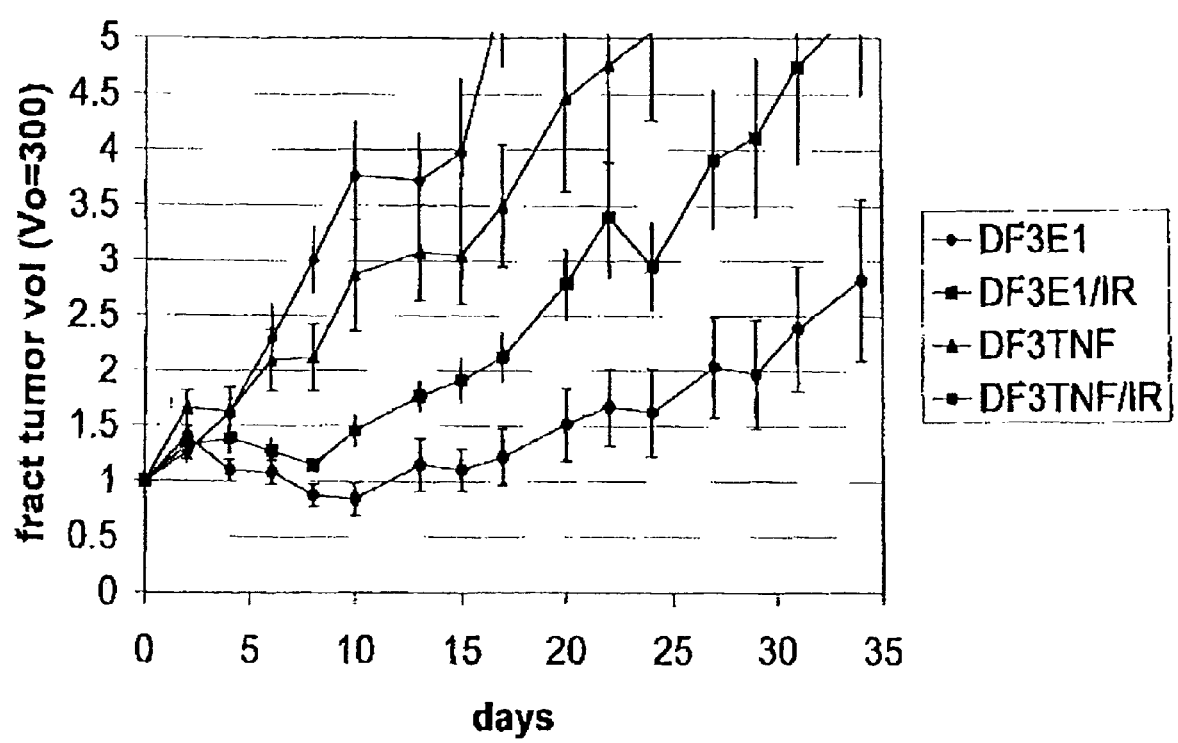
FIG. 1—DF3.TNF in Bic 1 cell lines. Fraction of tumor volume when Bic 1 xenografts are treated with null virus alone and TNF virus alone (DF3E1 and DF3TNF respectively) and in absence and presence of irradiation (DF3E1/IR and DF3TNF/IR respectively).

Replication-competent viruses offer certain advantages over replication-defective vectors for cancer gene therapy, namely, that replication-competent viruses have the capacity to spread throughout the tumor mass and to express therapeutic gene products. In the present invention, conditionally-replication competent viruses are constructed, which have a replication essential gene under the control of the DF3/MUC-1 promoter, such that the virus will replicate only in cells that express the DF3/MUC-1 antigen. The above constructs, in combination with known methods of gene and chemo/radiotherapy provide enhanced inhibition of tumor cell growth.

The results reported herein demonstrate that insertion of the DF3/MUC1 promoter upstream of a replication essential gene in a viral vector permits selective replication in MUC1-positive cells. The results also demonstrate that the viral construct induces selective lysis of tumor cells that express MUC1. Of importance, the replication-competent virus spread throughout the tumor mass, unlike a comparable replication-defective virus. These findings indicate that viral constructs with the capacity to selectively replicate in tumors have the potential for greater efficacy than that achieved with replication-defective viruses. In addition, the present invention further provides use of the DF3/MUC1 promoter to drive additional therapeutic transgenes, such as TNFα. Further, when combined with radiotherapy, antitumoral effects are increased.

II. Vectors and Regulatory Signals

The present invention provides improved viral vectors for gene therapy that use the DF3/MUC1 promoter to drive a replication essential viral gene. The vectors may, in and of themselves, be useful as therapeutics relying solely on their ability to replicate and destroy MUC1-expressing tumor cells. The vectors also can be used to deliver therapeutic genes under the control of appropriate eukaryotic regulatory machinery, including but not limited DF3/MUC1. In a particular embodiment, the present invention provides an adenovirus vector with a DF3/MUC1 promoter that drives the expression of a replication essential gene, E1A, and further has a therapeutic transgene under the control of a CMV promoter.

a. Viral Vectors

While the present invention is exemplified by use of adenovirus, the invention may be exploited using virtually any virus. The following viruses are considered suitable for use in accordance with the present invention.

i. Adenovirus

Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus et al., 1992).

ii. AAV Vectors

Adeno-associated virus (AAV) is an attractive vector system for use in the present invention as it has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

iii. Retroviral Vectors

Retroviruses have the ability to integrate their genes into the host genome, transferring a large amount of foreign genetic material, infecting a broad spectrum of species and cell types and of being packaged in special cell-lines (Miller, 1992).

In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iv. Other Viral Vectors

Other viral vectors may be employed in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for infection of various mammalian tumor cells (Friedmann, 1989; Ridgeway, 1988; Baichwal and Sugden, 1986; Coupar et al., 1988; Horwich et al., 1990).

b. Promoters

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

i. DF3/MUC1

In one aspect, the present invention utilizes the DF3/MUC1 promoter to drive expression of a viral, replication-essential gene. Optionally, the DF3/MUC1 promoter may also be used to drive the expression of therapeutic transgenes. The DF3/MUC1 antigen is a high molecular weight glycoprotein that is aberrantly overexpressed in human breast and other carcinomas (Kufe, 1984; Abe et al., 1987; Friedman et al., 1986) Nearly 80% of primary human breast carcinomas express high levels of MUC1 antigen (Kufe, 1984). Other studies have shown that human breast tumors express the MUC1 gene at the mRNA and protein levels in approximately 30-fold greater amounts than are found in normal breast tissue and benign lesions (Hareuveni et al., 1990).

The MUC1 gene contains seven exons and has been mapped to chromosome 1q21-24 9 (Lancaster et al., 1990; Swallow et al., 1987). It spans 4-7 kb's, depending on the number of conserved tandem repeats. Overexpression of the MUC1 gene in human breast cancer cells is regulated at the transcriptional level (Abe et al., 1990). The MUC1 promoter/enhancer region has been shown in the context of retroviral vector to direct expression of prodrug-activating enzymes and to confer selective killing of MUC1-positive human carcinoma cells (Manome et al., 1994). In other studies with replication-defective adenoviruses, the MUC1 promoter has been used to selectively express β-galactosidase or herpes simplex virus thymidine kinase (HSV-tk) in MUC1 positive breast cancer cells (Chen et al., 1995). Abe and Kufe (1990) have supported activation of the MUC1 gene in transformed mammary epithelium.

Although studies of MUC1 expression have been largely focused on breast tumor cells, other work has demonstrated that MUC1 is overexpressed in diverse carcinomas, including ovarian (Friedman et al., 1986), prostate (Ho et al., 1993), pancreas (Metzgar et al., 1984), and lung cancers (Jarrard et al., 1998). On the basis of these findings, and considering the potential for identifying elements in the MUC1 promoter that are activated in carcinomas, sequences responsible for MUC1 transcription were cloned from the 5' flanking region of the MUC1 gene. Cloning and characterization of the 5' flanking regions of the MUC1 gene has shown that expression of the gene is regulated mainly by sequences between positions −598 bp and −485 bp upstream from the transcription start site (Abe et al., 1993). Subsequent work using retroviral and adenoviral vectors demonstrated that the MUC1 promoter is functional in directing selective and efficient expression of heterologous genes in MUC1-positive cells (Manome et al., 1994; Chen et al., 1995).

ii. Other Promoters

Additional promoters may be utilized to drive various therapeutic transgenes, as discussed further below. A non-limiting list of such promoters are listed in Table 1.

TABLE 1

Other Promoter/Enhancer Elements

| Promoter/Enhancer | References |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| γ-Globin | Bodine and Ley, 1987; Perez-Stable and Constantini, 1990 |
| β-Globin | Trudel and Constantini, 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| a$_1$-antitrypsin | Latimer et al., 1990 |
| H2B (TH2B) Histone | Hwang et al., 1990 |
| Mouse or Type I Collagen | Ripe et al., 1989 |

TABLE 1-continued

Other Promoter/Enhancer Elements

| Promoter/Enhancer | References |
| --- | --- |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al, 1987; Gloss et al., 1987; Hirochika et al., 1987, Stephens and Hentschel, 1987; Glu et al., 1988 |
| Hepatitis B Virus | Bulla and Siddiqui, 1986; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al, 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 | iii. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iv. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998; Cocea, 1997). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

V. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997).

vi. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

vii. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

c. Therapeutic Genes

The present invention contemplates the use of a variety of different therapeutic transgenes. For example, genes encoding a tumor suppressor, an inhibitor of apoptosis, a cell cycle regulatory gene, a toxin, a cytokine, a ribosome inhibitory protein and interferons are contemplated as suitable genes that potentiate the inhibition of cancer cell growth according to the present invention.

i. Tumor Suppressors

The tumor suppressors function to inhibit excessive cellular proliferation. The inactivation of these genes destroys their inhibitory activity, resulting in unregulated proliferation. It is contemplated that toxins may be attached to antibodies that recognize mutant tumor suppressors or wild-type tumor suppressors. Alternatively, a toxin may be linked to all or part of the tumor suppressor. Exemplary tumor suppressors are p53, p16, and C-CAM, which are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al, 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Okamoto et al., 1994; Nobori et al., 1995; Orlow et al., 1994). Restoration of wild-type p16$^{INK4}$ function by transfection with a plasmid expression vector reduced colony formation by some human cancer cell lines (Okamoto, 1994).

Other genes that may be employed according to the present invention include Rb, APC, mda-7, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

ii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri). It is contemplated that any of these polypeptides, including TRAIL, or any other polypeptides that induce or promote apoptosis, may be operatively linked to a toxin, or that an antibody recognizing any of these polypeptides may also be attached to a toxin.

It will be appreciated by those of skill in the art that monoclonal or polyclonal antibodies specific for proteins that are preferentially expressed in metastatic or nonmetastatic cancer will have utilities in several types of applications. These may include the production of diagnostic kits for use in detecting or diagnosing human cancer. An alternative use would be to link such antibodies to therapeutic agents, such as chemotherapeutic agents, followed by administration to individuals with cancer, thereby selectively targeting the cancer cells for destruction. The skilled practitioner will realize that such uses are within the scope of the present invention.

iii. Interferons

Other classes of genes that are contemplated to be inserted into the vectors of the present invention include interferons, interleukins and cytokines. Inteferon-α, interferon-β, interferon-γ, interleukin 1 (IL-1), IL-2, IL-3, IL-4, IL-5, IL-6, IL-7, IL-8, IL-9, IL-10, IL-11, IL-12, IL-13, IL-14, IL-15, angiostatin, thrombospondin, endostatin, METH-1, METH-2, Flk2/Flt3 ligand, GM-CSF, G-CSF, M-CSF, and tumor necrosis factor (TNF).

iv. Cell Cycle Regulatory Genes

In another embodiment, the present invention utilizes an isolated nucleic acid segment comprising a cell cycle regulatory gene operatively linked to a DF3/MUC1 promoter region; transferring the nucleic acid segment into a cancer cell to obtain a transfected cell; and maintaining the cancer cell under conditions effective to express the cell cycle regulatory gene; wherein expression of the cell cycle regulatory gene inhibits proliferation of the cancer cell. In the practice of the method, the cell cycle regulatory gene operatively linked to an DF3/MUC1 promoter region may comprise a viral vector, a plasmid vector. In the present invention, it comprises an adenoviral vector. Further, the cell cycle regulatory gene may preferably encode Rb, p53, cell cycle dependent kinase, CDK kinase, cyclin or a constitutively active Rb gene product, or an antisense RNA.

V. Toxin Encoding Genes

In another embodiment, the present invention may be described as a method of inhibiting tumor cell growth comprising the steps of: obtaining an isolated nucleic acid segment comprising a toxin encoding gene. The genes may encode TNFα, gelonin, ricin A Chain, Pseudomonas exotoxin, diphtheria toxin, mitogillin, saporin, ribosome inhibitory protein.

vi. Oncogenes

Oncogenes are considered to be genes that, when mutated or activated, sponsor the development of cancer. Therapeutic intervention involves the inhibition of these gene products. For example, one may provide antisense or ribozymes which inhibit the transcription, processing or translation of an oncogene. Alternatively, single chain antibodies that encode products bind to and inhibit the oncogene can be utilized. Table 2 provides a list of suitable oncogene targets.

TABLE 2

| Gene | Source | Human Disease | Function |
|---|---|---|---|
| Oncogenes | | | |
| Growth Factors | | | FGF family member |
| HST/KS | Transfection | | |
| INT-2 | MMTV promoter Insertion | | FGF family member |
| INTI/WNTI | MMTV promoter Insertion | | Factor-like |
| SIS | Simian sarcoma virus | | PDGF B |

TABLE 2-continued

Oncogenes

| Gene | Source | Human Disease | Function |
|---|---|---|---|
| Receptor Tyrosine Kinases | | | |
| ERBB/HER | Avian erythroblastosis virus; ALV promoter insertion; amplified human tumors | Amplified, deleted Squamous cell Cancer; glioblastoma | EGF/TGF-/ Amphiregulin/ Hetacellulin receptor |
| ERBB-2/NEU/HER-2 | Transfected from rat Glioblastomas | Amplified breast, Ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoieis |
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; Familial medullary Thyroid cancer; Multiple endocrine Neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like transcription factor)/ PDGF receptor gene Fusion |
| TGF-receptor | | Colon carcinoma Mismatch mutation Target | |
| NONRECEPTOR TYROSINE KINASES | | | |
| ABL | Abelson Mul.V | Chronic myelogenous Leukemia translocation With BCR | Interact with RB, RNA polymerase, CRK, CBL |
| FPS/FES | Avian Fujinami SV; GA FeSV | | |
| LCK | Mul.V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE[1] | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and Drosophilia homology | Nevoid basal cell cancer Syndrome (Gorline Syndrome) | 12 transmembrane domain; signals through Gli homogue CI to antagonize hedgehog pathway |
| TAN-1 Notch homologue | Translocation | T-ALL | Signaling? |
| MISCELLANEOUS SIGNALING | | | |
| BCL-2 | Translocation | B-cell lymphoma | Apoptosis |
| CBL | Mu Cas NS-1 V | | Tyrosine-Phosphorylated RING finger interact Abl |

TABLE 2-continued

Oncogenes

| Gene | Source | Human Disease | Function |
|---|---|---|---|
| CRK | CT1010 ASV | | Adapted SH2/SH3 interact Abl |
| DPC4 | Tumor suppressor | Pancreatic cancer | TGF-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL In CML | Exchanger; protein Kinase |
| DBL | Transfection | | Exchanger |
| GSP | | | |
| NF-1 | Hereditary tumor Suppressor | Tumor suppressor Neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many Human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |
| ETS | Avian E26 virus | | DNA binding |
| EVII | MuL V promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-B family transcription factor |
| SK1 | Avian SKV770 Retrovirus | | Transcription factor |
| VHL | Heritable suppressor | Von Hippel-Landau Syndrome | Negative regulator or elongin; transcriptional elongation complex |
| WT-1 | | Wilm's tumor | Transcription factor |
| CELL CYCLE/DNA DAMAGE RESPONSE | | | |
| ATM | Hereditary disorder | Ataxia-telangiectasia | Protein/lipid kinase homology; DNA damage response |

TABLE 2-continued

Oncogenes

| Gene | Source | Human Disease | Function |
|---|---|---|---|
| | | | upstream in P53 pathway |
| BCL-2 | Translocation | Follicular lymphoma | Apoptosis |
| FACC | Point mutation | Fanconi's anemia group C (predisposition Leukemia | |
| MDA-7 | Fragile site 3p14.2 | Lung carcinoma | Histidine triad-related diadenosine 5,3-tetraphosphate asymmetric hydrolase |
| hMLI/MutL | | HNPCC | Mismatch repair; MutL Homologue |
| hMSH2/MutS | | HNPCC | Mismatch repair; MutS Homologue |
| hPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 Suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| P53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; Osteosarcoma; breast cancer; other sporadic cancers | Interact cyclin/cdk; regulate E2F transcription factor |
| XPA | | Xeroderma pigmentosum; skin cancer predisposition | Excision repair; photo-product recognition; zinc finger |

III. Cancer Therapy

A wide variety of cancer therapies are known to one of skill in the art. In the present invention the key type of therapy is gene therapy. This therapy may be used in combination with other therapies that are described later in the specification.

a. Viral Gene Therapy

One of the therapeutic embodiments contemplated by the present inventors is the intervention, at the molecular level, in the events involved in the tumorigenesis of some cancers. Specifically, the present inventors intend to provide, to a cancer cell, a viral vector capable of providing a therapeutic gene that can target cancer cells and inhibit their growth. The construct will contain DF3/MUC1 promoter that will enable the selective replication of the viral construct in DF3/MUC1 expressing cells.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, $1\times10^{12}$, or $1\times10^{13}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. An extensive list of possible routes is described elsewhere in the specification. For practically any tumor, systemic delivery is contemplated. This will prove especially important for attacking microscopic or metastatic cancer. Where discrete tumor mass, or solid tumor, may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

The method of treating cancer includes treatment of a tumor as well as treatment of the region near or around the tumor. In this application, the term "residual tumor site" indicates an area that is adjacent to a tumor. This area may include body cavities in which the tumor lies, as well as cells and tissue that are next to the tumor.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

b. Combination Cancer Therapy

A wide variety of cancer therapies, known to one of skill in the art, may be used in combination with the gene therapy contemplated in the present invention towards cancer cells expressing DF3/MUC1 antigen. Thus, in order to increase the effectiveness of the anticancer therapy using an expression construct coding therefor, it may be desirable to combine these compositions with other agents effective in the treatment of cancer such as but not limited to those described below.

For example, one can use the gene therapy in conjunction with radiation therapy, surgery, chemotherapy, immunotherapy, second gene therapy, and/or local heat therapy. Thus, one can use one or several of the standard cancer therapies existing in the art in addition with the gene-based therapies of the present invention. All therapies other than the gene therapy of the present invention will be referred to as "other cancer therapies".

The other cancer therapy may precede or follow the gene therapy by intervals ranging from minutes to days to weeks. In embodiments where the other cancer therapy and the gene therapy are administered together, one would generally ensure that a significant period of time did not expire between the time of each delivery. In such instances, it is contemplated that one would administer to a patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the other cancer therapy and the gene therapy will be required to achieve complete cancer cure. Various combinations may be employed, where the other cancer therapy is "A" and the gene therapy treatment is "B", as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations also are Contemplated.

i. Radiotherapeutic Agents

The present embodiment of the invention contemplates the use of radiation therapy along with the administration of an expression construct. Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Ionizing radiation causes DNA damage and cell killing, generally proportional to the dose rate. Ionizing radiation has been postulated to induce multiple biological effects by direct interaction with DNA or through the formation of free radical species leading to DNA damage. These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. Also, the phrase "effective expression-inducing dose of ionizing radiation" means that dose of ionizing radiation needed to stimulate or turn on a radiation responsive enhancer-promoter that is one embodiment of the present invention. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art. The amount of ionizing radiation needed in a given cell naturally depends upon the nature of that cell. As also used herein, the term "an effective dose" of ionizing radiation means a dose of ionizing radiation that produces an increase in cell damage or death when given in conjunction with a virus.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

ii. Surgery

Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy, such as with viral vector of the present invention. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

iii. Chemotherapeutic Agents

Agents that affect DNA function are defined as chemotherapeutic agents, for example, agents that directly cross-link DNA, agents that intercalate into DNA, and agents that lead to chromosomal and mitotic aberrations by affecting nucleic acid synthesis. Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. Other agents comtemplated are for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), or any analog or derivative variant of the foregoing.

iv. Immunotherapy

Immunotherapeutics, generally, rely on the use of immune effector cells and molecules to target and destroy cancer cells. The immune effector may be, for example, an antibody specific for some marker on the surface of a tumor cell. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. A gene encoding a toxic protein when transferred to cancer cells can cause cell death and apoptosis. The apoptotic cancer cells are scavenged by reticuloendothelial cells including dendritic cells and macrophages and presented to the immune system to generate anti-tumor immunity (Rovere et al., 1999; Steinman et al., 1999). Immune stimulating molecules may be provided as immune therapy: for example, cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with viral vector of the present invention will enhance anti-tumor effects. Immunotherapy may be of the following types: (i) Passive Immunotherapy which includes: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow; and/or (ii) Active Immunotherapy wherein an antigenic peptide, polypeptide or protein, or an autologous or allogenic tumor cell composition or "vaccine" is administered, generally with a distinct bacterial adjuvant (Ravindranath & Morton, 1991) and/or (iii) Adoptive Immunotherapy wherein the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

IV. Pharmaceutical Compositions and Routes of Administration

The present invention contemplates the use of viral constructs in the form of a pharmaceutical compositions. In general a pharmaceutical composition will comprise an effective amount of one or more proteinaceous sequence, nucleic acid, antibody or other agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one proteinaceous sequence, nucleic acid, antibody or other active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Compositions of the present invention comprise an effective amount of a protein or nucleic acid encapsulated in a liposome, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

The proteins and nucleic acids of the present invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Expression construct may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain embodiments the expression construct is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains-the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

In certain embodiments, the present invention concerns a composition comprising one or more lipids associated with at least one protein or nucleic acid. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally-occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

V. Kits

In still further embodiments, the present invention concerns kits for use in therapy for cancer. The treatment kits will thus comprise, in suitable container means, the viral construct such as an expression vector of the present invention.

The container means of the kits will generally include at least one vial, test tube, flask, bottle, syringe or other container means, into which the expression construct may be placed, and preferably, suitably aliquoted. The kits of the present invention will also typically include a means for containing the viral construct and any other reagent containers in close confinement for commercial sale. Such containers may include injection or blow-molded plastic containers into which the desired vials are retained.

Such kits will generally contain, in suitable container means, a pharmaceutically acceptable formulation of a polypeptide, peptide, biological functional equivalent, immunological fragment, domain, inhibitor, antibody, gene, polynucleotide, nucleic acid, complement, or vector expressing any of the foregoing in a pharmaceutically acceptable formulation. The kit may have a single container means, or it may have distinct container means for each compound.

When the components of the kit are provided in one or more liquid solutions, the liquid solution is an aqueous solution, with a sterile aqueous solution being particularly preferred. The expression construct compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means of the kits will generally include at least one vial, test tube, flask, bottle, syringe or other container means, into which the expression construct may be placed, and preferably, suitably aliquoted.

Irrespective of the number or type of containers, the kits of the invention may also comprise, or be packaged with, an instrument for assisting with the injection/administration or placement of the ultimate construct within the body of an animal. Such an instrument may be a syringe, pipette, forceps, or any such medically approved delivery vehicle.

VI. EXAMPLES

Example 1

Materials and Methods

Cell culture. Bic-1 and Seg-1 human esophageal adenocarcinoma cell lines (gift from Dr. David Beer, University of Michigan) were grown in Dulbecco's Modified Eagle Medium (DMEM, Gibco RL, Grand Island, N.Y.) supplemented with 10% fetal bovine serum, L-glutamine, 100 µg/ml streptomycin and 100 units/ml penicillin. The cell line was incubated at 37° C. in 7% $CO_2$.

Viral replication and TNFα production in Bic-1 cells. $2 \times 10^5$ Bic-1 and Seg-1 cells were plated in separate 6-well tissue culture dishes overnight. The cells were infected with 0.001 MOI of Ad.DF3.E1A.CMV.TNF (Ad.DF3.TNF) for 2 hours in serum-free medium. Then the medium was exchanged with 4 ml normal growth medium. Conditioned medium was then harvested at days 0, 1, 2, and 5 and stored at −80° C. Human tumor necrosis factor α enzyme linked immunosorbant assay (hTNFα ELISA, R&D Systems Minneapolis, Minn.) was used according to the manufacturer's instructions to quantify human TNFα levels within the conditioned medium.

Generation of xenografts. All animal investigations were performed under approved Animal Care Committee (IACUC) protocols at the University of Chicago. Bic-1 xenografts were produced by injecting $5 \times 10^6$ cells into the subcutaneous space in the right hind limb of athymic nude mice. Seg-1 xenografts were produced in a similar manner with $3 \times 10^6$ cells also in athymic nude mice. Xenografts were measured thrice weekly according the formula length×width×height/2. Each tumor volume measurement was compared to its volume at day 0 and therefore expressed as a fractional tumor volume.

Viral replication and TNFα production in Bic-1 xenografts. Following the generation of Bic-1 and Seg-1 xenografts in athymic nude mice, the animals were randomized to receive either Ad.DF3.TNF or the null virus at a dose of $2 \times 10^8$ particle units (pu). The virus was administered as a single dose on day 0. Animals were sacrificed and tumors harvested on day 7. Tumors were snap frozen in liquid nitrogen and stored at −80° C. Tumors were thawed and homogenized in 500 µl RIPA buffer (150 mM NaCl, 10 mM Tris-HCl, pH 7.5, 5 mM EDTA, pH 7.5, 10 µg/ml aprotinin, 5 µg/ml leupeptin, and 100 mM PMSF) utilizing the Brinkman Polytron homogenizer (Kinematica, AG, Littau, Switzerland) for 30 seconds on ice. After 4 freeze/thaw cycles, tumor homogenates were centrifuged at 4° C. at 10000 rpm for 10 minutes utilizing the RC5C refrigerated centrifuge (Sorvall Instruments Inc.) with the SS-34 rotor. The pellet was discarded and a standard R&D protein assay using the Bradford dye technique was performed on the supernatant. Human TNF in the supernatant was quantified using hTNFα ELISA (R&D Systems, Minneapolis, Minn.) according to the manufacturer's instructions.

Xenograft histology. Bic-1 and Seg-1 xenografts generated in athymic nude mice treated with either Ad.DF3.GFP or Ad.DF3.TNF at a dose of $2 \times 10^8$ pfu and then were followed for 21 days. The mice were sacrificed following CO2 narcosis and the tumors harvested. Representative tumor sections were dissected and snap frozen in OCT. 4 mm sections were cut on Probe-On slides. Bic-1 and Seg-1 xenografts treated with Ad.DF3.GFP were examined using immunofluorescence microscope for green fluorescence protein (GFP). Bic-1 and Seg-1 xenografts treated with Ad.DF3.TNF were stained with DAPI and also examined using the immunofluorescence microscope with the 10× and 40× objectives.

Xenograft regrowth studies. Following the generation of Bic-1 and Seg-1 xenografts, animals with a mean xenograft volume of 260 mm3 were randomized to one of 6 groups: buffer alone, buffer+radiation, Ad.DF3.Null, null virus+radiation, Ad.DF3.TNF, and Ad.DF3.TNF+radiation. The adenoviral vectors were administered as a single dose $2 \times 10^8$ pfu directly within the tumor with a Hamilton syringe in 10 μl buffer through a single entry point to 5 separate sites. 10 μl buffer alone was administered in a similar manner to animals in the first 2 groups. Tumor beds were irradiated using a Pantak PMC 1000 x-ray generator operating at 150 kV and 25 mA at a dose rate of 192 cGy/minute. Animals were shielded with lead except for the tumor bearing hind limb. The Bic-1 xenografts received a dose of 4Gy (Gray) each day on days 0, 1, 2, and 3 (total 16 Gy) and the Seg-1 xenografts a dose of 5Gy each day on days 0, 1, 2, 3, and 4 (total 25 Gy) determined according to their radiosensitivity curves. Groups were compared according to their mean fractional tumor volumes.

Example 2

Results

Selective TNFα production in DF3/MUC1 producing cells. Bic-1 and Seg-1 human esophageal adenocarcinoma cells were incubated with Ad.DF3.TNF at 0.001 MOI for 2 hours. Human TNFα ELISA of the conditioned medium indicates similar infection rates in both cell lines demonstrated by the equivalent TNFα production at days 0, 1 and 2. However, by day 5, the 15-fold increase in TNFα produced by the Bic-1 (DF3+) cell line compared to the Seg-1 (DF3−) cell line indicates viral replication, increased TNFα gene expression and subsequently greater TNFα production in the DF3/MUC1-producing cell line compared to the non-producers.

Selective TNFα production in DF3/MUC1 producing xenografts. Following the generation of Bic-1 and Seg-1 xenografts in athymic nude mice, each was treated with single intratumoral dose of Ad.DF3.TNF ($2 \times 10^8$ pu). Human TNFα ELISA of the tumor homogenates demonstrates a 50-fold increase in TNFα production in the Bic-1 xenografts as compared to the Seg-1 xenografts. These findings indicate enhanced viral replication and greater TNFα gene expression in the DF3/MUC1 producing Bic-1 xenografts as compared with the DF3/MUC1 non-producers.

Enhanced viral replication in DF3/MUC1 producing xenografts. Following the generation of Bic-1 and Seg-1 xenografts in athymic nude mice, each tumor type was treated with either the vector containing the TNFα gene, Ad.DF3.TNF, or a null virus tagged with green fluorescence protein (GFP), Ad.DF3.GFP. Tumors harvested at 21 days following intratumoral administration of a single dose of vector ($2 \times 10^8$ pu) were examined histologically. Enhanced green fluorescence staining in Ad.DF3.GFP treated Bic-1 xenograft sections indicates continued viral replication in the DF3/MUC1 producing xenografts as compared to the Seg-1 xenografts. Loss of nuclear architecture following DAPI staining in Ad.DF3.TNF treated Bic-1 sections indicates enhanced viral replication and TNFα-induced apoptosis in the DF3/MUC1 producers compared to the non-producing Seg-1 xenografts. These findings further demonstrate the selectivity of the DF3/MUC1 promoter to direct viral replication and therapeutic gene expression.

Figure 2:
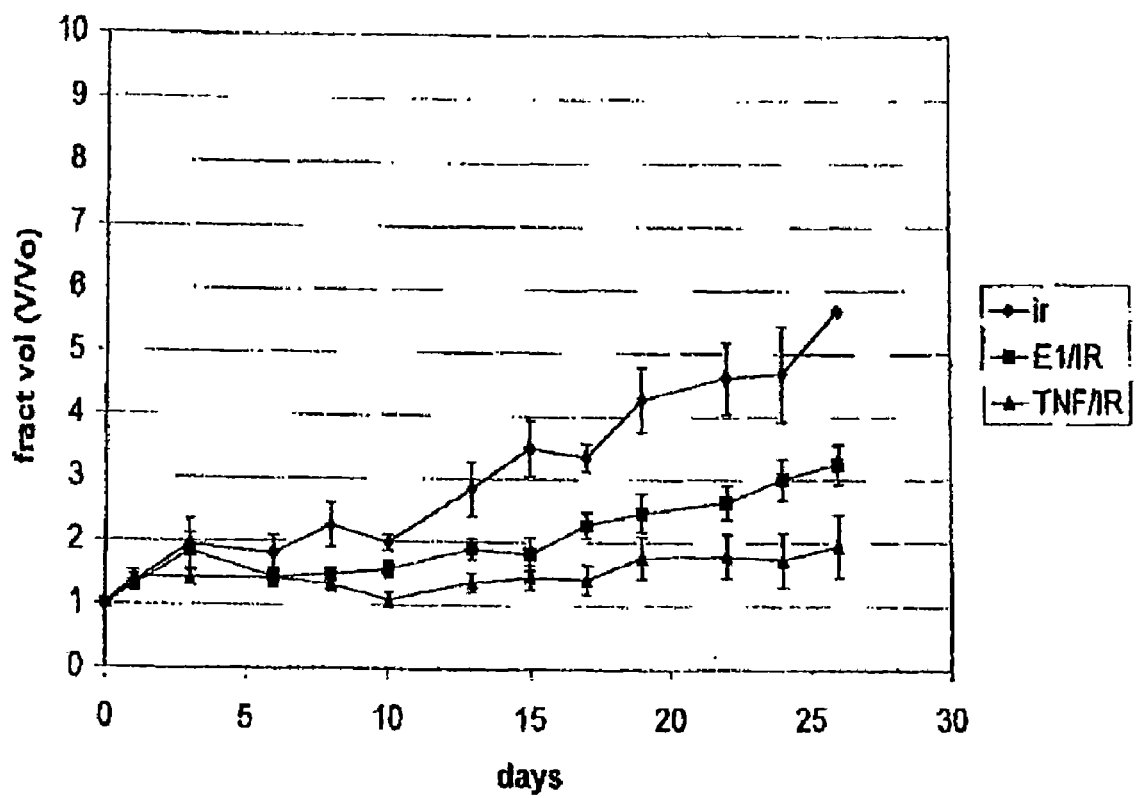
FIG. 2—Ad.DF3.TNF in Bic 1 cell lines. The fraction of tumor volume when Bic xenograft is treated with null virus in presence of irradiation (E1/IR) and when treated with virus TNF in presence of irradiation (TNF/IR). This is compared with tumor volumes obtained when Bic xenograft is treated with irradiation alone.
Figure 3:
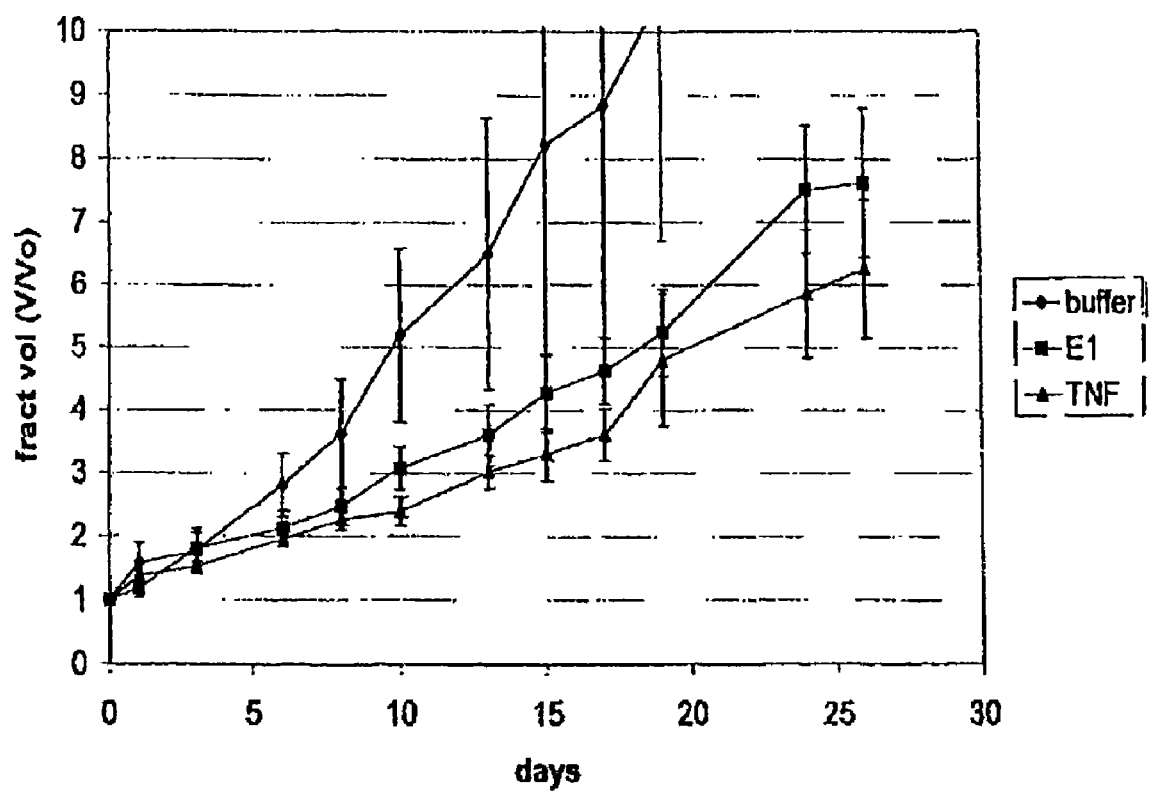
FIG. 3—Ad.DF3.TNF in Bic 1 cell lines. The fraction of tumor volume when Bic xenograft is treated with buffer, null virus (E1) and TNF.

Enhanced TNFα production in Bic-1 xenografts increases tumor radiosensitivity. To determine the effect of selective viral replication and enhanced TNF gene expression in vivo, athymic nude mice bearing (DF3−) Seg-1 xenografts were randomized to one of six treatment groups. Following administration of each group's appropriate treatment, mean fractional tumor volumes were charted and found to demonstrate two clusters of regrowth curves. The clustering of curves suggests no activation of the DF3/MUC1 promoter and therefore no adenoviral replication in the DF3/MUC1 non-producing Seg-1 xenografts. The absence of a differential effect following radiation also suggests a lack of TNF.alpha. gene expression in the Seg-1 xenografts. In comparison, Bic-1 xenografts treated with either the null virus or the TNF virus alone, demonstrated a small antitumor effect compared to buffer alone treated xenografts. TNF.alpha. expression in the Ad.DF3.TNF alone treated xenografts did not change the regrowth pattern of the xenografts compared to Ad.DF3.Null alone treated animals. However, when the Ad.DF3.TNF+IR treated animals were compared with the Ad.DF3.Null+IR treated animals, the TNF.alpha. expression significantly reduced tumor regrowth (FIG. 1). A comparison of tumor fraction volume when Bic 1 xenograft treated with null virus and TNF virus in the absence and presence of irradiation is shown in FIG. 3 and FIG. 2, respectively.

These findings taken together show that TNFα expression in the Ad.DF3.TNF treated Bic-1 xenografts has little antitumor effect alone, but enhances tumor radiosensitivity when combined with ionizing radiation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abe and Kufe, *J. Cell. Physiol.*, 143:226-231, 1990.
Abe and Kufe, *J. Immunol.*, 139:257-261, 1987.
Abe and Kufe, *Proc. Nat'l Acad. Sci. U.S.A.*, 90:282-286, 1993.
Angel et al., *Cell*, 49:729, 1987.
Angel et al., *Mol. Cell. Biol.*, 7:2256, 1987.
Atchison and Perry, *Cell*, 46:253, 1986.
Atchison and Perry, *Cell*, 48:121, 1987.
Baichwal and Sugden, *In: Gene Transfer*, New York, Plenum Press, 117-148, 1986.
Bakhshi, et al., *Cell*, 41(3):899-906, 1985.
Banerji et al., *Cell*, 27(2 Pt 1):299-308, 1981.
Banerji et al., *Cell*, 33(3):729-740, 1983.
Berkhout et al., *Cell*, 59:273-282, 1989.

Bett, Haddara, Prevec, Graham, *Proc. Nat'l Acad. Sci. U.S.A.*, 91:8802-8806, 1994.
Blanar et al., *E.M.B. O. J.*, 8:1139, 1989.
Blomer et al., *J. Virol.*, 71(9):6641-6649, 1997.
Bodine and Ley, *E.M.B.O. J*, 6:2997, 1987.
Boothman et al., *Cancer Res.*, 49(11):2871-8, 1989.
Borek, *Carcinog. Compr. Surv.*, 10:303-16, 1985.
Boshart et al., *Cell*, 41:521, 1985.
Bosze et al., *E.M.B.O. J*, 5(7):1615-1623, 1986.
Braddock et al., *Cell*, 58:269, 1989.
Bulla and Siddiqui, *J. Virol.*, 62:1437, 1986.
Caldas et al., *Nat. Genet.*, 8(1):27-32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Nat'l Acad. Sci. U.S.A.*, 94(8):3596-601, 1997.
Chang et al., *Mol. Cell. Biol.*, 9:2153, 1989.
Chatterjee et al., *Proc. Nat'l Acad. Sci. U.S.A.*, 86:9114, 1989.
Chen et al., *J. Clin. Invest.*, 96:2775-2782, 1995.
Cheng et al., *Cancer Res.*, 54(21):5547-5551, 1994.
Choi et al., *Cell*, 53:519, 1988.
Cleary and Sklar, *Proc. Nat'l Acad. Sci. USA*, (21):7439-7443, 1985.
Cleary et al., *J. Exp. Med.*, 164(1):315-320, 1986.
Cocea, *Biotechniques*, 23(5):814-816, 1997.
Cohen et al., *J. Cell. Physiol.*, 5:75, 1987.
Costa et al., *Mol. Cell. Biol.*, 8:81-90, 1988.
Coupar et al., *Gene*, 68:1-10, 1988.
Cripe et al., *EMBO J.*, 6:3745, 1987.
Culotta and Hamer, *Mol. Cell. Biol.*, 9:1376-1380, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Edbrooke et al., *Mol. Cell. Biol.*, 9:1908-1916, 1989.
Edlund et al., *Science*, 230:912-916, 1985.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Friedman et al., *Cancer Res.*, 46:5189-5194, 1986.
Friedmann, *Science*, 244:1275-1281, 1989.
Fujita et al., *Cell*, 49:357, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Goodboum and Maniatis, *Proc. Nat'l Acad. Sci. U.S.A.*, 85:1447, 1988.
Goodboum et al., *Cell*, 45:601, 1986.
Greene et al., *Immunology Today*, 10:272, 1989
Grosschedl and Baltimore, *Cell*, 41:885, 1985.
Grunhaus et al., *Seminar in Virology*, 200(2):535-546, 1992.
Haj-Ahmad and Graham, *Virology*, 153:22-34, 1986.
Hareuveni et al., *Proc. Nat'l Acad. Sci. U.S.A.*, 87:9498-9502, 1990.
Haslinger and Karin, *Proc Nat'l Acad. Sci. U.S.A.*, 82:8572, 1985.
Hauber and Cullen, *J. Virology*, 62:673, 1988.
Heise and Kim, *J. Clin. Invest.*, 105:847-851, 2000.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Ho et al. *Cancer Res.*, 53:641-651, 1993.
Holbrook et al., *Virology*, 157:211, 1987.
Holistein et al., *Science*, 253(5015):49-53, 1991.
Horlick and Benfield, *Mol. Cell. Biol.*, 9:2396, 1989.
Horwich et al., *Virol.*, 64:642-650, 1990.
Huang et al., *Cell*, 27:245, 1981.
Hug et al., *Mol. Cell. Biol.*, 8:3065, 1988.
Hussussian et al., *Nat. Genet.*, 8(1):15-21, 1994.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jarrard et al., *Cancer Res.*, 58:5582-5588, 1998.
Jaynes et al., *Mol. Cell. Biol.*, 8:62, 1988.
Johnson et al., *Mol. Cell. Biol.*, 9:3393, 1989.
Kadesch and Berg, *Mol. Cell. Biol.*, 6:2593, 1986.
Kamb et al., *Nat. Genet.*, 8(1):23-2, 1994.
Karin et al., *Mol. Cell. Biol.*, 7:606, 1987.
Katinka et al., *Cell*, 20:393, 1980.
Katinka et al., *Nature*, 290:720, 1981.
Kawamoto et al., *Mol. Cell. Biol.*, 8:267, 1988.
Kerr et al., *Br. J. Cancer*, 26(4):239-257, 1972.
Kiledjian et al., *Mol. Cell. Biol.*, 8:145, 1988.
Klamut et al., *Mol. Cell. Biol.*, 10:193, 1990.
Koch et al, *Mol Cell. Biol.*, 9:303, 1989.
Kriegler and Botchan, *In: Eukaryotic Viral Vectors*, Cold Spring Harbor, Cold Spring Harbor Laboratory, N.Y., 1982.
Kriegler and Botchan, *Mol. Cell. Biol.*, 3:325, 1983.
Kriegler et al., *Cell*, 38:483, 1984.
Kriegler et al., *In: Cancer Cells 2/Oncogenes and Viral Genes*, Cold Spring Harbor: Cold Spring Harbor Laboratory, 1984.
Kriegler et al., *In: Gene Expression*, Hamer and Rosenberg, New York, 1983.
Kufe et al., *Hybridoma*, 3:223-232.
Kuhl et al., *Cell*, 50:1057, 1987.
Kunz, et al., *Nucl. Acids Res.*, 17:1121, 1989.
Lambert and Borek, *J. Nat'l Cancer Inst.*, 80(18):1492-1497, 1988.
Lancaster et al. *Biochem. Biophys. Res. Commun.*, 173:1019-1029, 1990.
Larsen et al., *Proc. Natl. Acad. Sci. U.S.A.*, 83:8283, 1986.
Laspia et al., *Cell*, 59:283, 1989.
Latimer et al., *Mol. Cell. Biol.*, 10:760, 1990.
Laughlin et al, *J. Virol.*, 60(2):515-524, 1986.
Lebkowski et al., *Mol. Cell Biol.*, 8(10):3988-3996, 1988.
Lee et al., *Nature*, 294:228, 1981.
Levenson et al., *Hum. Gene Ther.*, 9(8):1233-6, 1998.
Levinson et al., *Nature*, 295:79, 1982.
Lin, et al., *Mol. Cell. Biol.*, 10:850, 1990.
Luria et al., *E.M.B.O. J.*, 6:3307, 1987.
Lusky and Botchan, *Proc. Nat'l Acad. Sci. U.S.A.*, 83:3609, 1986.
Lusky et al., *Mol. Cell. Biol.* 3:1108, 1983.
Macejak and Sarnow, *Nature*, 353:90-94, 1991.
Majors and Varmus, *Proc. Nat'l Acad. Sci. U.S.A.*, 80:5866, 1983.
Mann et al., *Cell*, 33:153-159, 1983.
Manome et al., *Cancer Res.*, 54:5408-5413, 1994.
Marsters et al., *Recent Prog. Horm. Res.*, 54:225-234, 1999.
McLaughlin et al., *J. Virol.*, 62(6):1963-1973, 1988.

McNeall et al., *Gene,* 76:81, 1989.
Metzgar et al., *Proc. Nat'l Acad. Sci. USA,* 81:5242-5246, 1984.
Miksicek et al., *Cell,* 46:203, 1986.
Miller et al., *Am. J. Clin. Oncol.,* 15(3):216-221, 1992.
Miyatake et al., *Gene. Ther.,* 6:564-572, 1999.
Mordacq and Linzer, *Genes and Dev.,* 3:760, 1989.
Moreau et al., *Nucl. Acids Res.,* 9:6047, 1981.
Musesing et. al., *Cell,* 48:691, 1987.
Muzyczka, *Curr. Top Microbiol. Immunol.,* 158:97-129, 1992.
Naldini et al., *Science,* 272(5259):263-267, 1996.
Ng et al., *Nuc. Acids Res.,* 17:601, 1989.
Nicolas and Rubinstein, In: *Vectors: A survey of molecular cloning vectors and their uses,* Stoneham: Butterworth, pp. 494-513, 1988.
Nobori et al., *Nature,* 368(6473):753-756, 1994.
Okamoto et al., *Proc. Nat'l Acad. Sci. USA,* 1(23):11045-11049, 1994.
Omitz et al., *Mol. Cell. Biol.* 7:3466, 1987.
Ondek et al., *E.M.B.O. J.,* 6:1017, 1987.
Orlow et al., *Cancer Res.,* 54(11):2848-2851, 1994.
Palmiteretal., *Cell,* 29:701, 1982.
Paskind et al., *Virology,* 67:242-248, 1975.
Pech et al., *Mol. Cell. Biol.,* 9:396, 1989.
Pelletier and Sonenberg, *Nature,* 334:320-325, 1988.
Perez-Stable and Constantini, *Mol. Cell. Biol.,* 10:1116, 1990.
Picard and Schaffner, *Nature,* 307:83, 1984.
Pinkert et al., *Genes and Dev.,* 1:268, 1987.
Ponta et al., *Proc. Nat'l Acad. Sci. U.S.A.,* 82:1020, 1985.
Porton et al., *Mol. Cell. Biol.,* 10:1076, 1990.
Queen and Baltimore, *Cell,* 35:741, 1983.
Quinn et al., *Mol. Cell. Biol.,* 9:4713, 1989.
Redondo et al., *Science,* 247:1225, 1990.
Reisman and Rotter, *Mol. Cell. Biol.,* 9:3571, 1989.
Remington's Pharmaceutical Sciences, 18th Ed. Mack Printing Company, pp. 1289-1329, 1990.
Resendez Jr. et al., *Mol. Cell. Biol.,* 8:4579, 1988.
Ridgeway, In: *Vectors: A survey of molecular cloning vectors and their uses,* Stoneham: Butterworth, pp. 467-492, 1988.
Ripe et al., *Mol. Cell. Biol.,* 9:2224, 1989.
Rittling et al., *Nuc. Acids Res.,* 17:1619, 1989.
Rodriguez et al., *Cancer Res.,* 57:2559-2563, 1997.
Rosen et al., *Cell,* 41:813, 1988.
Rosenberg et al., *Ann. Surg.,* 210(4):474-548, 1989
Rosenberg et al., *N. Engl. J. Med.,* 319:1676, 1988.
Rovere et al., *Arthritis Rheum.,* 42(7):1412-1420, 1999.
Sakai et al., *Genes and Dev.,* 2:1144, 1988.
Satake et al., *J. Virology,* 62:970, 1988.
Schaffner et al., *J. Mol. Biol.,* 201:81, 1988.
Searle et al., *Mol. Cell. Biol.,* 5:1480, 1985.
Serrano et al., *Nature,* 366:704-707, 1993.
Serrano et al., *Science,* 267(5195):249-252, 1995.
Sharp and Marciniak, *Cell,* 59:229, 1989.
Shaul and Ben-Levy, *E.M.B.O. J.,* 6:1913, 1987.
Sherman et al., *Mol. Cell. Biol.,* 9:50, 1989.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Steinman et al., *Hum Immunol,* 60(7):562-567, 1999.
Stephens and Hentschel, *Biochem. J,* 248:1, 1987.
Stuart et al., *Nature,* 317:828, 1985.
Sullivan and Peterlin, *Mol. Cell. Biol.,* 7:3315, 1987.
Swallow et al., *Ann. Hum. Genet.,* 51:289-294, 1987.
Swartzendruber and Lehman, *J. Cell. Physiology,* 85:179, 1975.
Takebe et al., *Mol. Cell. Biol.,* 8:466, 1988.
Tavernier et al., *Nature,* 301:634, 1983.
Taylor and Kingston, Mol. Cell. Biol., 10: 165, 1990a.
Taylor and Kingston, *Mol. Cell. Biol.,* 10:176, 1990b.
Taylor et al., *J. Biol. Chem.,* 264:15160, 1989.
Temin, In: *Gene Transfer,* New York: Plenum Press, pp. 149-188, 1986.
Thiesen et al., *J. Virology,* 62:614, 1988.
Tratschin et al., *Mol. Cell. Biol.,* 4:2072-2081, 1984.
Treisman, *Cell,* 42:889, 1985.
Tronche et al., *Mol. Biol. Med.,* 7:173, 1990.
Tronche et al., *Mol. Cell. Biol.,* 9:4759, 1989.
Trudel and Constantini, *Genes and Dev.,* 6:954, 1987.
Tsujimoto and Croce, *Proc. Nat'l Acad. Sc.i U.S.A.* 83(14): 5214-5218, 1986.
Tsujimoto et al., *Science,* 228(4706):1440-1443, 1985.
Tyndall et al., *Nuc. Acids. Res.,* 9:6231, 1981.
Uchida, *Urology,* 58(2 Suppl 1):132-139, 2001.
Vannice and Levinson, *J. Virology,* 62:1305, 1988.
Varda-Bloom, *Gene Ther.,* 8(11):819-827, 2001.
Vasseur et al., *Proc. Nat'l Acad. Sci. U.S.A.,* 77:1068, 1980.
Wang and Calame, *Cell,* 47:241, 1986.
Weber et al., *Cell,* 36:983, 1984.
Weinberg, "Tumor suppressor genes," *Science,* 254(5035): 1138-1146, 1991.
Weinberger et al., *Mol. Cell. Biol.,* 8:988, 1984.
Winoto and Baltimore, *Cell,* 59:649, 1989.
Witte et al., *Cancer Res.,* 49(18):5066-72, 1989.
Yutzey et al., *Mol. Cell. Biol.,* 9:1397, 1989.
Zufferey et al., *Nat. Biotechnol.,* 15(9):871-875, 1997.
U.S. Pat. No. 4,683,202
U.S. Pat. No. 4,797,368
U.S. Pat. No. 5,139,941
U.S. Pat. No. 5,925,565
U.S. Pat. No. 5,928,906
U.S. Pat. No. 5,935,819
U.S. Pat. No. 5,994,136
U.S. Pat. No. 6,013,516

What is claimed is:

1. A method for enhancing radiosensitivity of a cancer cell expressing DF3/MUC1 glycoprotein, comprising directly administering to the cancer cell an adenoviral vector comprising a first polynucleotide sequence encoding E1A operably linked to a MUC1 promoter and a second polynucleotide sequence encoding TNF-α operably linked to a CMV promoter; and irradiating the cancer cell.

2. The method of claim 1 wherein the cancer cell is a bladder cell, a breast cell, a lung cell, a colon cell, a prostate cell, a pancreatic cell, a stomach cell, an ovarian cell, or a lymphatic cell.

* * * * *

SEQUENCE LISTING

<160> NUMBER OF SEQ ID NOS: 1

<210> SEQ ID NO 1
<211> LENGTH: 1725
<212> TYPE: DNA
<213> ORGANISM: Homo sapiens -continued

```
<400> SEQUENCE: 1
gcttccgtgc gcctagagcg cagcctgcga ctgcgggacc caacaaccac gtgctgccgc      60
ggcctgggat agcttcctcc cctctggcac tgctgccgca cacacctctt ggctgtcgcg     120
cattacgcac ctcacgtgtg cttttgcccc cgcctacgtg cctacctgtc cccaatacca     180
ctctgctccc caaaggatag ttctgtgtcc gtaaatccca ttctgtcacc ccacctactc     240
tctgcccccc ccttttttgt tttgagacgg agtcttgctc tgtcgcccag gctggagtgc     300
aatggcgcga tctcggctca ctgcaacctc cgcctccgg gttcaagcga ttctcctgcc      360
tcagcctcct gagtagctgg ggttacagcg cccgccacca cgctcggcta attttttgtag    420 tttttagtag agacgaggtt tcaccatctt ggccaggctg tcttgaacc cctgaccttg     480 tgatccactc gcctcggcct tccaaagtgt tgggattacg ggcgtgacga ccgtgccacg     540
cccgatctgc ctcttaagta cataacggcc cacacagaac gtgtccaact cccccgccca     600
cgttccaacg tcctctccca catacctcgg tgccccttcc acatacctca ggaccccacc     660
cgcttagctc catttcctcc agacgccacc accacgcgtc ccggagtgcc cctcctaaa     720 gctcccagcc gtccaccatg ctgtgcgttc ctccctccct ggccacggca gtgacccttc     780
tctcccgggc cctgcttccc tctcgcgggc tctcgctgcc tcacttaagc agcgctgccc     840
ttactcctct ccgcccggtc cgagcggccc ctcagcttgc gcggcccagc ccgcaaggc     900 tcccggtgac cactagaggg cgggaggagc tcctggccag tggtggagag tggcaaggaa    960
ggaccctagg gttcatcgga gcccaggttt actcccttaa gtggaaattt cttccccac   1020 tccctccttg gctttctcca aggagggaac ccaggctgct ggaaagtccg gctggggcgg   1080
ggactgtggg tttcagggta gaactgcgtg tggaacggga cagggagcgg ttagaagggt   1140
ggggctattc cgggaagtgg tgggggagg gagcccaaaa ctagcaccta gtccactcat   1200
tatccagccc tcttatttct cggccccgct ctgcttcagt ggacccgggg agggcgggga   1260
agtggagtgg gagacctagg ggtgggcttc ccgaccttgc tgtacaggac ctcgacctag   1320
ctggctttct tccccatccc cacgttagtt gttgccctga ggctaaaact agagcccagg   1380
ggccccaagt tccagactgc ccctccccc tccccggag ccagggagtg gttggtgaaa    1440
gggggaggcc agctggagaa caaacgggta gtcaggggt tgagcgatta gagcccttgt   1500
accctaccca ggaatggttg gggaggagga ggaagaggta ggaggtaggg gaggggcgg   1560 ggttttgtca cctgtcacct gctccggctg tgcctagggc gggcgggcgg ggagtggggg   1620
gaccggtata aagcggtagg cgcctgtgcc cgctccacct ctcaagcagc cagcgcctgc   1680
ctgaatctgt tctgcccct ccccacccat ttcaccacca ccatg                    1725
```